(12) United States Patent
Cattell

(10) Patent No.: US 6,180,351 B1
(45) Date of Patent: Jan. 30, 2001

(54) CHEMICAL ARRAY FABRICATION WITH IDENTIFIER

(75) Inventor: Herbert F. Cattell, Mountain View, CA (US)

(73) Assignee: Agilent Technologies Inc., Palo Alto, CA (US)

(*) Notice: Under 35 U.S.C. 154(b), the term of this patent shall be extended for 0 days.

(21) Appl. No.: 09/359,536

(22) Filed: Jul. 22, 1999

(51) Int. Cl.$^7$ .............................. C12Q 1/68; G06F 12/00
(52) U.S. Cl. .................................. 435/6; 707/200
(58) Field of Search .................. 712/200; 707/200; 435/6, 287.2, 7.5; 901/6, 16

(56) References Cited

U.S. PATENT DOCUMENTS

| | | | |
|---|---|---|---|
| 5,281,540 | 1/1994 | Merkh et al. | 436/530 |
| 5,314,829 | * 5/1994 | Coles et al. | 436/165 |
| 5,404,523 | 4/1995 | DellaFera et al. | 395/650 |
| 5,812,793 | 9/1998 | Shakib et al. | 395/200.31 |
| 5,837,454 | * 11/1998 | Cozzette et al. | 435/6 |

FOREIGN PATENT DOCUMENTS

363223557 * 9/1988 (JP).

* cited by examiner

*Primary Examiner*—John S. Brusca
*Assistant Examiner*—Young J. Kim
(74) *Attorney, Agent, or Firm*—Gordon Stewart

(57) ABSTRACT

A method of generating an addressable array of biopolymers, such as DNA probes, on a substrate. The method includes receiving from a remote station, information on a layout of the array and an associated first identifier. A local identifier is generated corresponding to the first identifier and associated array, the local identifier being shorter in length than the corresponding first identifier. The addressable array is fabricated on the substrate in accordance with the received layout information. A first copy of the local identifier is applied to the substrate or a housing carrying the substrate. The fabricated array and the first copy of the local identifier are shipped to a remote user station. A method at the corresponding user station, and apparatus and computer program products useful at either station, are further provided.

22 Claims, 2 Drawing Sheets

CHEMICAL ARRAY FABRICATION WITH IDENTIFIER

FIELD OF THE INVENTION

This invention relates to arrays, particularly biopolymer arrays (such polynucleotide arrays, and particularly DNA arrays) which are useful in diagnostic, screening, gene expression analysis, and other applications.

BACKGROUND OF THE INVENTION

Arrays of biopolymers, such as arrays of peptides or polynucleotides (such as DNA or RNA), are known and are used, for example, as diagnostic or screening tools. Such arrays include regions (sometimes referenced as features or spots) of usually different sequence biopolymers arranged in a predetermined configuration on a substrate. The arrays, when exposed to a sample, will exhibit a pattern of binding which is indicative of the presence and/or concentration of one or more components of the sample, such as an antigen in the case of a peptide array or a polynucleotide of particular sequence in the case of a polynucleotide array. The binding pattern can be detected by interrogating the array, for example, by observing a fluorescence pattern on the array following exposure to a fluid sample in which all potential targets (for example, DNA) in the sample have been labeled with a suitable fluorescent label.

Biopolymer arrays can be fabricated using either in situ synthesis methods or deposition of the previously obtained biopolymers. The in situ synthesis methods include those described in U.S. Pat. No. 5,449,754 for synthesizing peptide arrays, as well as WO 98/41531 and the references cited therein for synthesizing polynucleotides (specifically, DNA). Such in situ synthesis methods can be basically regarded as iterating the sequence of depositing droplets of: (a) a protected monomer onto predetermined locations on a substrate to link with either a suitably activated substrate surface (or with a previously deposited deprotected monomer); (b) deprotecting the deposited monomer so that it can now react with a subsequently deposited protected monomer; and (c) depositing another protected monomer for linking. Different monomers may be deposited at different regions on the substrate during any one iteration so that the different regions of the completed array will have different desired biopolymer sequences. One or more intermediate further steps may be required in each iteration, such as oxidation and washing steps.

The deposition methods basically involve depositing biopolymers at predetermined locations on a substrate which are suitably activated such that the biopolymers can link thereto. Biopolymers of different sequence may be deposited at different regions of the substrate to yield the completed array. Washing or other additional steps may also be used. Typical procedures known in the art for deposition of polynucleotides, particularly DNA such as whole oligomers or cDNA, are to load a small volume of DNA in solution in one or more drop dispensers such as the tip of a pin or in an open capillary and, touch the pin or capillary to the surface of the substrate. Such a procedure is described in U.S. Pat. No. 5,807,522. When the fluid touches the surface, some of the fluid is transferred. The pin or capillary must be washed prior to picking up the next type of DNA for spotting onto the array. This process is repeated for many different sequences and, eventually, the desired array is formed. Alternatively, the DNA can be loaded into a drop dispenser in the form of an inkjet head and fired onto the substrate. Such a technique has been described, for example, in PCT publications WO 95/25116 and WO 98/41531, and elsewhere. This method has the advantage of non-contact deposition. Still other methods include pipetting and positive displacement pumps such as the Biodot equipment (available from Bio-Dot Inc., Irvine Calif., USA).

In array fabrication, the quantities of DNA available for the array are usually very small and expensive. Sample quantities available for testing are usually also very small and it is therefore desirable to simultaneously test the same sample against a large number of different probes on an array. These conditions require use of arrays with large numbers of very small, closely spaced spots. Due to the precision required, and to maintain costs low, while end users may design their own array layout it will often be desirable to have the arrays fabricated at a fabrication facility and then shipped to the end user. Since the end user designed the array, they will have array layout information available to them at their own location. However, when an array corresponding to the array layout is received from the fabrication facility, some type of identification should be provided on the array substrate or a housing containing the array which allows matching that array to the layout information, since array layout information in some form is used to meaningfully interpret the information obtained from interrogating the array. Unique identifiers and their generation have been previously described, such as in U.S. Pat. No. 5,812,793, U.S. Pat. No. 5,404,523, and the references cited therein. Such unique identifiers (often referred to as "Globally Unique Identifiers" or "GUIDs", or "Universally Unique Identifiers" or "UUIDs") can, for example, include a network card identification which is specific to that card, along with a time and local counter number, and other components. Use of such unique identifiers in association with array layouts generated at the same or different locations, would virtually eliminate the possibility of the same identifier being associated with different array layouts. However, such unique identifiers typically require 128 bit data string. A string of such length when written, for example, as a bar code, typically takes up about 3 to 4 cm, which is more room than is often available on a substrate adjacent a typical array (which may be less than about 1 cm in any dimension).

It would be desirable then, if there was a way in which unique identifiers, such as GUIDs or UUIDs could still be associated with array layouts but without requiring, on an array or its housing, an amount of space (whether physical or data string length) normally occupied when such unique identifiers are written.

SUMMARY OF THE INVENTION

The present invention then, realizes that unique identifiers can still be associated with an array, without requiring the same amount of space on the array or its housing, which are normally required by such unique identifiers. In particular, the present invention realizes that this can be accomplished by using a second identifier of shorter length than a corresponding unique identifier, and which is associated in some manner with the unique identifier.

In one aspect then, the present invention provides a method of generating an addressable array of chemical moieties on a substrate. The chemical moieties may particularly include biopolymers, for example polynucleotides (such as DNA or RNA) or peptides. The method includes obtaining information on a layout of the array (such as from a remote site or locally, for example from a local memory). An identifier corresponding to the array layout information is also obtained. The addressable array is fabricated on the substrate in accordance with the layout information. The identifier is applied to the substrate carrying the array (such as, for example, writing the identifier directly onto the substrate).

In another aspect, the present invention provides a method of generating an addressable array of chemical moieties on a substrate. The method includes receiving from a remote station, information on a layout of the array and an associated unique identifier. A local identifier is generated which corresponds to the unique identifier and associated array, the local identifier being shorter in length than the corresponding unique identifier. The addressable array is fabricated on the substrate in accordance with the received layout information. A first copy of the local identifier is applied to the substrate or a housing carrying the substrate. The fabricated array and the first copy of the local identifier are then shipped to a remote station.

Note that in the foregoing aspect, the association of the local identifier with the unique identifier, in order to recover the array layout information, could take place in a number of ways. For example, the method may further include forwarding a second copy of the corresponding local identifier to a remote station such that the local identifier is associated with the corresponding unique identifier. This forwarding may be in a manner such that the association of the local identifier and corresponding unique identifier, is indicated. For example, a second copy of the local identifier is communicated to a remote station following receipt of the corresponding unique identifier communicated from the remote station, or by applying both to a same medium (which provides physical association; such as packaging containing the fabricated array) which can then be shipped to the remote station. In an alternative example, this association could be stored at the same location at which the array is fabricated, and accessed from the remote location upon receipt of the array and first copy of the local identifier. Thus, either the remote location (such as a requesting station) or elsewhere (such as the fabrication location) could maintain a mappings (such as in a database or file) of unique identifiers each in association with the corresponding local identifier. Any such a database may optionally also contain the layout information.

Note that in the above discussion, the remote station from which array layout information is received can be the same or different from the remote station to which the second copy of the local identifier is provided. Thus, a fabricated array and the first copy of the local identifier on the array or its housing, can be shipped to a remote end user which is different from the remote station which provided the array layout information (the "requester"). In this manner, such a different end user can still use the array, simply by obtaining the layout information corresponding to the unique identifier, from the requestor or from elsewhere.

In another aspect of the present invention, a method of generating addressable arrays of chemical moieties on multiple substrates, at a central fabrication station is provided. In this aspect, information on a layout of an array and an associated unique identifier is received at the central fabrication station from each of multiple remote locations. For each received unique identifier and associated array, a local identifier is generated corresponding to the unique identifier and associated array, the local identifier being shorter in length than the corresponding unique identifier. An addressable array is fabricated on a substrate in accordance with each received layout information. A first copy of each local identifier is applied to the substrate or a housing carrying the substrate, which substrate carries the array corresponding to the generated local identifier. Optionally, each fabricated array and the first copy of the corresponding local identifier is shipped to one or more of the remote stations. In this aspect, the central fabrication station may then deal with each of the remote stations in any of the same manners described above. When a database of the above described type is stored at the central fabrication station, this may include the referenced information from any one or more, or all, of the multiple remote stations.

In another aspect of the present invention, there is provided a method of using an addressable array of chemical moieties on a substrate. The method includes receiving from a remote fabrication station, the addressable array and a first copy of a local identifier carried on the array substrate or a housing for the array substrate, which local identifier corresponds to a unique identifier and associated array and is shorter in length than the unique identifier. The local identifier is read from the array substrate or housing and the corresponding unique identifier retrieved. Information on the layout of the associated array may be retrieved from a memory using the retrieved local identifier. This method can include providing any of those items received, or receiving any of those items provided, in the methods of generating an array described above. The providing or receiving may be by any means, either communication for only information, or shipping for physical items (including media carrying data or information). This method may further optionally include exposing a sample to the array, and interrogating the array following the exposure to the sample. Any of these steps may be performed at a first requesting station (that is, the same station).

The foregoing method of using aspect may also optionally include any of a number of additional features. For example, in response to receipt of a second copy of the local identifier, saving the local identifier in a memory in association with the corresponding unique identifier. Also, interrogation of the array may be controlled, or information obtained from interrogation of the array processed, in accordance with retrieved array layout information. The array may be exposed to a test sample and, following interrogation of the array, the test sample then evaluated for the presence of a target based on results from the interrogation.

In another aspect of the invention, there is provided an apparatus for producing an addressable array of chemical moieties on a substrate. This apparatus can include the components required to carry out one or more of the above array generation methods. Such an apparatus may include a processor to receive information on a layout of the array and a unique identifier associated with the array, and which generates a local identifier corresponding to the received unique identifier and associated array, the local identifier being shorter in length than the corresponding unique identifier. An array fabricator is also included to fabricate the addressable array on the substrate in accordance with the received layout information. A writing system is provided to apply a first copy of the local identifier to the substrate or a housing carrying the substrate. This writing system (which may have one or more of the same or different type writers) may also write to a medium (such as a label) a shipping address to which the addressable array is to be shipped, as well as the second copy of the local identifier and the corresponding unique identifier to another one or the same medium.

In a further aspect of the present invention, there is provided an apparatus for receiving an addressable array of chemical moieties on a substrate, which can execute one or more of the methods of using described above. The apparatus may include a first reader which reads a first copy of a local identifier carried on an array substrate or a housing for the array substrate, which local identifier corresponds to a unique identifier associated with the array and is shorter in length than the unique identifier. A processor retrieves the corresponding unique identifier using the read local identifier, and which retrieves information on the layout of the associated array from a memory using the retrieved unique identifier. The apparatus may also further optionally include a scanner to interrogate the array after it has been exposed to a sample.

The present invention further provides a computer program product including a computer readable storage medium having a computer program stored on it. The program can control, when loaded into a computer, an apparatus for producing an addressable array of chemical moieties on a substrate as described above, so that it will execute one or more of the steps required by it. In one aspect, the program performs the step of receiving from a remote station, information on a layout of the array and an associated unique identifier. A local identifier is generated corresponding to the unique identifier and associated array, the local identifier being shorter in length than the corresponding unique identifier. Fabrication of the addressable array on the substrate is controlled in accordance with the received layout information. A first copy of the local identifier is applied to the substrate or a housing carrying the substrate.

In another aspect of the invention there is provided a computer program product including a computer readable storage medium having a computer program on it. The program can control, when loaded into a computer, an apparatus for receiving an addressable array of chemical moieties on a substrate, so that it will execute one or more of the steps required by it. In one particular aspect, the program performs the steps of receiving a local identifier from an array substrate or housing, the local identifier being shorter in length than a corresponding unique identifier. A second copy of the local identifier is received and in response to receiving the second copy, storing the local identifier in association with the corresponding unique identifier. The unique identifier is retrieved using the corresponding local identifier received from the array substrate or housing. Information on the layout of the associated array is retrieved from a memory using the retrieved unique identifier. Optionally, the program may also control interrogation of the array or processing information obtained from interrogation of the array, either in accordance with retrieved array layout information.

The various aspects of the present invention can provide any one or more of a number of useful benefits. For example, unique identifiers, such as GUIDs or UUIDs can still be associated with array layouts with the attendant advantages of using such unique identifiers, but without requiring, on an array or its housing, an amount of space (whether physical or data string length) normally occupied when such unique identifiers are written. Further, providing identifiers on the substrate particularly facilitates fabrication and enables multiple arrays with respective physically associated identifiers on a single substrate.

BRIEF DESCRIPTION OF THE DRAWINGS

Embodiments of the invention will now be described with reference to the drawings in which.

To facilitate understanding, identical reference numerals have been used, where practical, to designate identical elements that are common to the figures.

DETAILED DESCRIPTION OF THE INVENTION

Throughout the present application, unless a contrary intention appears, the following terms refer to the indicated characteristics. A "biopolymer" is a polymer of one or more types of repeating units. Biopolymers are found in biological systems and particularly include peptides or polynucleotides, as well as such compounds composed of or containing amino acid or nucleotide analogs or non-nucleotide groups. This includes polynucleotides in which the conventional backbone has been replaced with a non-naturally occurring or synthetic backbone, and nucleic acids in which one or more of the conventional bases has been replaced with a synthetic base capable of participating in Watson-Crick type hydrogen bonding interactions. Polynucleotides include single or multiple stranded configurations, where one or more of the strands may or may not be completely aligned with another. While probes and targets of the present invention will typically be single-stranded, this is not essential. A "nucleotide" refers to a sub-unit of a nucleic acid and has a phosphate group, a 5 carbon sugar and a nitrogen containing base, as well as analogs of such sub-units. Specifically, a "biopolymer" includes DNA (including cDNA), RNA and oligonucleotides, regardless of the source. An "oligonucleotide" generally refers to a nucleotide multimer of about 10 to 100 nucleotides in length, while a "polynucleotide" includes a nucleotide multimer having any number of nucleotides. A "biomonomer" references a single unit, which can be linked with the same or other biomonomers to form a biopolymer (for example, a single amino acid or nucleotide with two linking groups one or both of which may have removable protecting groups). A biomonomer fluid or biopolymer fluid reference a liquid containing either a biomonomer or biopolymer, respectively (typically in solution). An "array", unless a contrary intention appears, includes any one or two dimensional arrangement of addressable regions bearing a particular chemical moiety to moieties (for example, biopolymers such as polynucleotide sequences) associated with that region. An array is "addressable" in that it has multiple regions of different moieties (for example, different polynucleotide sequences) such that a region (a "feature" or "spot" of the array) at a particular predetermined location (an "address") on the array will detect a particular target or class of targets (although a feature may incidentally detect non-targets of that feature). In the present case, the target will be in a mobile phase (typically fluid), while probes ("target probes") will be bound to the substrate at the various regions. An "array layout" refers to one or more characteristics of the array, such as feature positioning, feature size, and some indication of a moiety at a given location. "Hybridizing" and "binding", with respect to polynucleotides, are used interchangeably. "Binding efficiency" refers to the productivity of a binding reaction, measured as either the absolute or relative yield of binding product formed under a given set of conditions in a given amount of time. "Hybridization efficiency" is a particular sub-class of binding efficiency, and refers to binding efficiency in the case where the binding components are polynucleotides. It will also be appreciated that throughout the present application, that words such as "upper", "lower" are used in a relative sense only. A "set" may have one type of member or multiple different types. "Fluid" is used herein to reference a liquid. By one item being "remote" from another is referenced that they are at least in different buildings, and may be at least one, at least ten, or at least one hundred miles apart. Reference to a singular item, includes the possibility that there are plural of the same items present. By one thing being "remote" from the other, is referenced that they are at least in different buildings, and may be at least one mile apart, or at least ten, twenty, or even at least one hundred miles apart. By one item being "forwarded" from one place to another includes the possibility of that item being sent by any means possible for that type of item. Thus, in the case where that item is only information, forwarding of that item includes the possibility of it being communicated or being written onto a medium which is then shipped (that is, physically transported). However, physical items (such as a substrate or storage medium) cannot be communicated. Similarly, by an item being "received" includes the possibility of it being received by any means possible for that type of item. By "communicated" or similar terms, is referenced electronic communication on any type of device by which information can be transmitted or received (for example, over a network such as a telephone or WAN, satellite, radio, or the like, or any combination of those).

Figure 1:
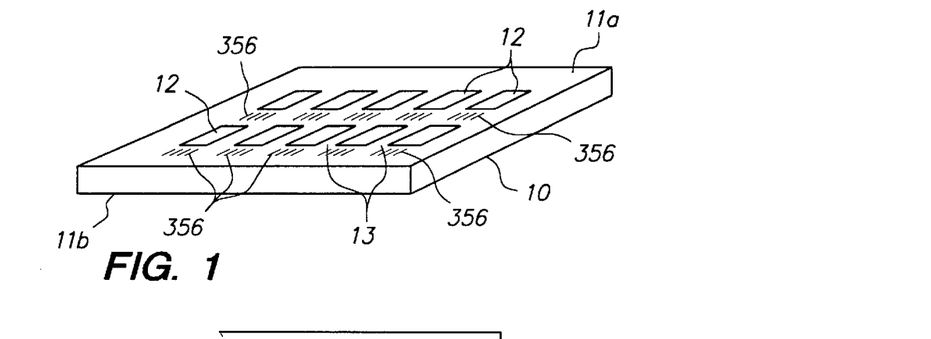
FIG. 1 illustrates a substrate carrying multiple arrays and a local identifier associated with each, such as may be fabricated or used by methods and apparatus of the present invention.
Figure 2:
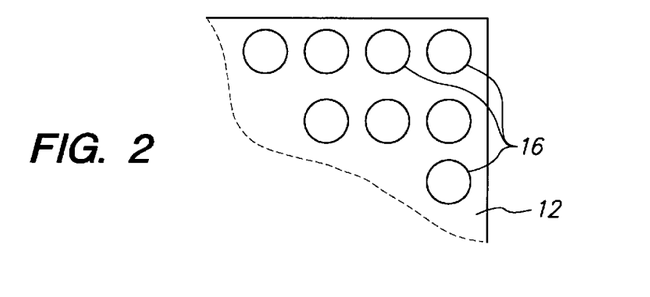
FIG. 2 is an enlarged view of a portion of FIG. 1 showing multiple spots or regions of one array.
Figures 3, 5:
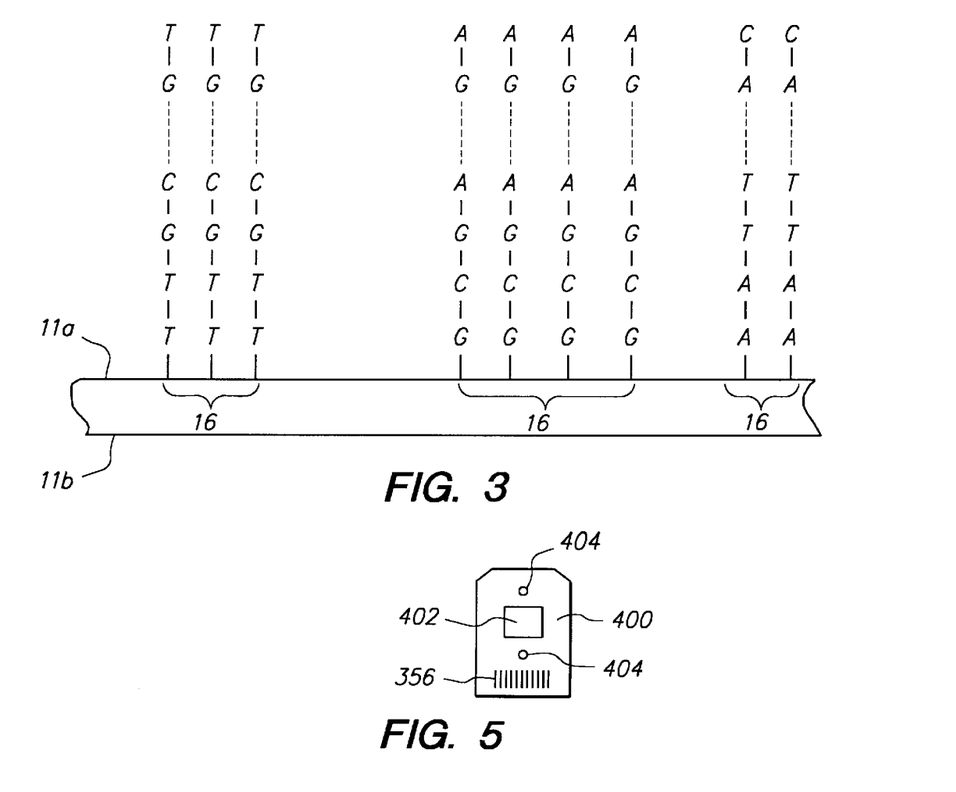
FIG. 3 is an enlarged illustration of a portion of the substrate of FIG. 1.
FIG. 5 illustrates an array housing carrying a local identifier.

Referring first to FIGS. 1–3, typically methods and apparatus of the present invention generate or use a contiguous planar substrate 10 carrying one or more arrays 12 disposed across a first surface 11a of substrate 10 and separated by areas 13. The arrays on substrate 10 can be designed for testing any type of sample, whether a trial or reference sample, or a combination of them. While ten arrays 12 are shown in FIG. 1 and the different embodiments described below may use substrates with particular numbers of arrays, it will be understood that substrate 10 and the embodiments to be used with it, may use any number of desired arrays 12. Similarly, substrate 10 may be of any shape, and any apparatus used with it adapted accordingly. Depending upon intended use, any or all of arrays 12 may be the same or different from one another and each will contain multiple spots or features 16 of biopolymers in the form of polynucleotides. A typical array may contain from more than ten, more than one hundred, more than one thousand or ten thousand features, or even more than from one hundred thousand features. All of the features 16 may be different, or some or all could be the same. Each feature carries a predetermined moiety (which includes the possibility of mixtures of moieties, such as mixtures of polynucleotides). It will be appreciated though, that there need not be any space separating arrays 12 from one another, nor features 16 within an array from one another. Note from FIG. 1 that there is a local identifier in the form of local bar code 356, physically associated with each array 12 by virtue of being adjacent to that array. Local bar codes 356 will be the same for identical arrays 12 (that is, arrays having the same layout), but will be different for arrays with different layouts.

Figure 4:
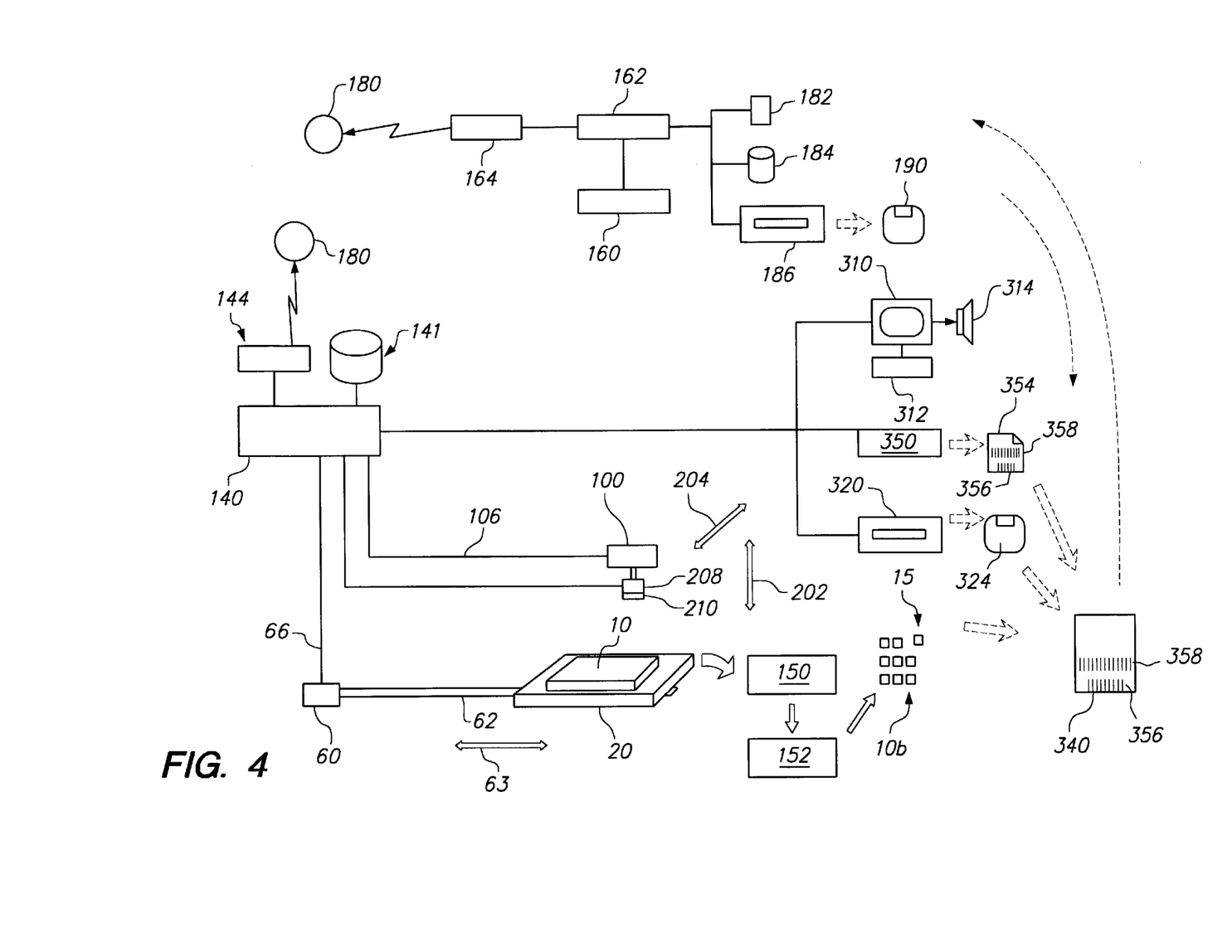
FIG. 4 is a schematic illustrating both an apparatus of the present invention for producing an addressable array, together with an apparatus of the present invention for receiving an addressable array, and their use.

Referring to FIG. 4 the apparatus includes a substrate station 20 on which can be mounted a substrate 10. Substrate station 20 can include a vacuum chuck connected to a suitable vacuum source (not shown) to retain a substrate 10 without exerting too much pressure thereon, since substrate 10 is often made of glass. A dispensing head 210 is retained by a head retainer 208. Head 210 can be positioned to face substrate station 20 by a positioning system. The positioning system includes a carriage 62 connected to substrate station 20, a transporter 60 controlled by a processor 140 through line 66, and a second transporter 100 controlled by processor 140 through line 106. Transporter 60 and carriage 62 are used execute one axis positioning of either of the stations 20 or 30, facing the dispensing head 210 by moving them in the direction of arrow 63, while transporter 100 is used to provide two axis adjustment of the position of head 210 in a vertical direction 202 or in the direction 204. Further, once substrate station 20 has been positioned facing head 210, the positioning will be used to scan head 208 across a mounted substrate 14, typically line by line (although other scanning configurations could be used). However, it will be appreciated that both transporters 60 and 100, or either one of them, with suitable construction, can be used to perform any necessary positioning (including the foregoing scanning) of head 210 with respect to any of the stations. Thus, when the present application recites "positioning" one element (such as head 210) in relation to another element (such as one of the stations 20, or 30) it will be understood that any required moving can be accomplished by moving either element or a combination of both of them.

The apparatus further includes a display 310, speaker 314, and operator input device 312. Operator input device 312 may, for example, be a keyboard, mouse, or the like. Processor 140 has access to a memory 141, and controls head 210 (specifically, the activation of the ejectors therein), operation of the positioning system, operation of each jet in print head 210, and operation of a writing system (as described below), display 310 and speaker 314. Memory 141 may be any suitable device in which processor 140 can store and retrieve data, such as magnetic, optical, or solid state storage devices (including magnetic or optical disks or tape or RAM, or any other suitable device). Any processor described herein may include a general purpose digital microprocessor (such as typically used in a programmable computer) suitably programmed to execute all of the steps required by it, or any hardware or software combination which will perform the required functions. Processor 140 also has access through a communication module 144 to a communication channel 180 to communicate with a remote station. Communication channel 180 may, for example, be a Wide Area Network ("WAN"), telephone network, satellite network, or any other suitable communication channel.

Head 210 may be of a type commonly used in an ink jet type of printer and may, for example, have multiple drop dispensing orifices communicating with one or more chambers for holding either previously obtained polynucleotide solution (deposition method), or a solution of a polynucleotide monomer (for in situ method). Ejectors are positioned in the one or more chambers, each opposite a corresponding orifice. For example, each ejector may be in the form of an electrical resistor operating as a heating element under control of processor 140 (although piezoelectric elements could be used instead). Each orifice with its associated ejector and portion of the chamber, defines a corresponding pulse jet. In this manner, application of a single electric pulse to an ejector causes a droplet to me dispensed from a corresponding orifice. Certain elements of the head 210 can be adapted from parts of a commercially available thermal inkjet print head device available from Hewlett-Packard Co.

as part no. HP51645A. One suitable head configuration is described in more detail in U.S. patent application entitled "A MULTIPLE RESERVOIR INK JET DEVICE FOR THE FABRICATION OF BIOMOLECULAR ARRAYS" Ser. No. 09/150,507 filed Sep. 9, 1998.

As is well known in the ink jet print art, the amount of fluid that is expelled in a single activation event of a pulse jet, can be controlled by changing one or more of a number of parameters, including the orifice diameter, the orifice length (thickness of the orifice member at the orifice), the size of the deposition chamber, and the size of the heating element, among others. The amount of fluid that is expelled during a single activation event is generally in the range about 0.1 to 1000 pL, usually about 0.5 to 500 pL and more usually about 1.0 to 250 pL. A typical velocity at which the fluid is expelled from the chamber is more than about 1 m/s, usually more than about 10 m/s, and may be as great as about 20 m/s or greater. As will be appreciated, if the orifice is in motion with respect to the receiving surface at the time an ejector is activated, the actual site of deposition of the material will not be the location that is at the moment of activation in a line-of-sight relation to the orifice, but will be a location that is predictable for the given distances and velocities.

The sizes of the spots can have widths (that is, diameter, for a round spot or an equivalent area for a non-round spot) in the range from a minimum of about 10 $\mu$m to a maximum of about 1.0 cm. In embodiments where very small spot sizes or feature sizes are desired, material can be deposited according to the invention in small spots whose width is in the range about 1.0 $\mu$m to 1.0 mm, usually about 5.0 $\mu$m to 500 $\mu$m, and more usually about 10 $\mu$m to 200 $\mu$m.

The above described general apparatus may be used to fabricate arrays in which the desired previously obtained moieties are directly deposited at the desired locations on substrate 10 (such as the deposition of polynucleotides), or may be used to synthesize the desired moieties (such as polynucleotides) in an in situ synthesis method such as described above for the in situ synthesis of polynucleotides on an array. Modifications to the above apparatus which may be made depending on the array formation method are described in co-pending U.S. patent applications entitled "FABRICATING BIOPOLYMER ARRAYS" by M. Caren et al., Ser. No. 09/302,922 filed Apr. 30, 1999, and "PREPARATION OF BIOPOLYMER ARRAYS" by A. Schleifer et al., Ser. No. 09/302,899 filed Apr. 30, 1999. Those references and all other references cited in the present application, are incorporated herein by reference.

It should be specifically understood though, that the present invention is not limited to pulse jet type deposition systems as part of the fabricator. In particular, any type of array fabricating apparatus can be used as the fabricator, including those such as described in U.S. Pat. No. 5,807,522, or apparatus which may employ photolithographic techniques for forming arrays of moieties, such as described in U.S. Pat. No. 5,143,854 and U.S. Pat. No. 5,405,783, or any other suitable apparatus which can be used for fabricating arrays of moieties.

A writing system which is under the control of processor 140, includes a writer in the form of a printer 150 which can write a local identifier to substrate 10 by printing it in the form of local bar code 356 (or alternatively on a housing carrying the substrate) in association with a corresponding array 12. The writing system further includes a data writer/reader 320 (such as an optical or magnetic disk drive) which can write data to a portable computer readable storage medium (such as an optical or magnetic disk), and includes a printer 350 which can print labels with a shipping address as well as unique and local bar codes onto one or more labels.

The above described components in FIG. 4 represent an apparatus for producing an addressable array, which is sometimes references herein as a "fabrication station". FIG. 4 also illustrates an apparatus for receiving an addressable array, in particular a single "user station", which is remote from the fabrication station. The user station includes a processor 162, a memory 184, a scanner 160 which can interrogate an array, a second bar code reader 182, data writer/reader 186 (which may be capable of reading/writing to the same type of media as writer/reader 320), and a communication module 264 which also has access to communication channel 180. Memory 184 can be any type of memory such as those used for memory 141. Scanner 160 can be any suitable apparatus for interrogating an array, such as one which can read the location and intensity of fluorescence at each feature of an array following exposure to a fluorescently labeled sample. For example, such a scanner may be similar to the GENEARRAY scanner available from Hewlett-Packard, Palo Alto, Calif. Scanner 160 also includes though, a first bar code reader to read a first copy of each local bar code 356 appearing on substrate 10, while second bar code reader 182 can read both a second copy of each local bar code 356 appearing on a media such as label on a package 340, as well as the corresponding unique bar code 358.

It will be understood that there may be multiple such user stations, each remote from the fabrication station and each other, in which case the fabrication station acts as a central fabrication station (that is, a fabrication station which services more than one remote user station at the same or different times). One or more such user stations may be in communication with the fabrication station at any given time. It will also be appreciated that processors 140 and 162 can be programmed from any computer readable medium carrying a suitable computer program. For example, such a medium can be any memory device such as those described in connection with memory 141, and may be read locally (such as by reader/writer 320 in the case of processor 140 or reader/writer 186 in the case of processor 162) or from a remote location through communication channel 180.

In operation of the apparatus, processor 162 at the illustrated user station has access to array layout information in memory 184. This layout information could have been manually input by a user through a suitable user interface device (not shown) communicating with processor 162, or could have been read of a portable storage medium 190 by reader/writer 186, or received from a remote location through communication channel 180 and communication module 164. Processor 162 then generates a unique identifier, such as in the format described in U.S. Pat. No. 5,812,793. For the "network address" portion of the GUID, processor 162 can use a the unique network card identification returned from a network card (not shown) communicating with processor 162 and currently assigned by network card manufacturers. However, other unique identifications could be used instead, such as unique identifications now being provided in each microprocessor of the PENTIUM III class, manufactured by Intel Corporation, CA. This unique identifier is saved in memory 184 in association with the corresponding array layout.

The array layout information and associated unique identifier, are then forwarded to the fabrication station. This can be done, for example, by communicating such information from the remote user station through communication channel 180 or by writer/reader 186 writing a disk 190 carrying the array layout information and associated unique identifier which is then shipped to the fabrication station. In either event, this data is received at the fabrication station such as through communication module 144 or by reader/writer 320 reading disk 190. At this point processor 140 generates a local identifier corresponding to the unique identifier and the associated array which will be fabricated from the received layout information. The local identifier is shorter in length than the corresponding unique identifier. That is, for a 128 bit unique identifier, the corresponding local identifier might be about no more than ½ the size, or no more than ¼ or even no more than ¹⁄₁₆ the size. For example, the local identifier may contain one or two letters representing the fabricator's name (16 bits) and data representing some other alphanumeric or other language designation. This local identifier is stored in memory 141 in association with the corresponding unique identifier and array layout.

Processor 140 then controls the fabricator, as described above, to generate the one or more arrays on substrate 10 which correspond to the received array layout information and unique identifier. Substrate 10 carrying the arrays 12, is then sent to writer 150 which, under control of processor 140, writes a first copy of the local identifier 356 corresponding to each array onto substrate 10 in association with that array (by being physically close to it in the manner shown in FIG. 1). The substrate 10 is then sent to a cutter 152 where each individual array 12 and its associated local identifier 356 are separated from the remainder of the substrate 10, as indicated by reference number 10b, to provide multiple array units 15. For each array unit 15, printer 350, under control of processor 140, prints as bar codes on a same label 354 a second copy of the corresponding local identifier 356 as well as the corresponding unique identifier 358. Printer 350 may also print a shipping address on that or another label (which may have been received from the remote user station or elsewhere). The array unit 15 is placed in package 340 onto which label 350 is applied so that the second copy of the corresponding local identifier 356 and unique identifier are visible from the outside of package 340. Alternatively, label 350 can be placed inside package 340 along with the corresponding array unit 15. In either manner, the second copy of the local identifier 356 and corresponding unique identifier 358, are physically associated with the corresponding array. The resulting package is then shipped to a remote user station (which may be the same or different from the remote user station from which the array layout information and unique identifier were received).

The above sequence can be repeated at the fabrication station as desired for multiple substrates 10 in turn.

It will be appreciated that the fabrication station acts as a central fabrication station for each of multiple remote user stations, in the same manner as described above. Whether or not the fabrication station acts as a central fabrication station, it can optionally maintain a database of received unique identifiers, each in association with the corresponding local identifier and/or corresponding array layout information.

At the user station, the resulting package is then received from the remote fabrication station. Second reader 182 is used to read from package 340 the second copy of the local identifier 356. In this case, the corresponding unique identifier 358 is retrieved by second reader 182 also reading it from the package. These are stored in memory 184 in association with one another. A sample, for example a test sample, is exposed to the array 12 on the array unit 15 received in package 340. The array is then inserted into scanner 160 and interrogated by it to obtain interrogation results (such as information representing the fluorescence pattern on the array 12). The first reader also reads the first copy of the local identifier 356 present on the array substrate 10 in association with the corresponding array 12. Processor 162 retrieves the array layout information for the array corresponding to this read first copy of the local identifier 356, by accessing from memory 184 the corresponding unique identifier (which was previously saved in association with the corresponding unique identifier). From the unique identifier, processor 184 can obtain the array layout information since the array layout information was also previously saved in memory 184 in association with the corresponding unique identifier.

Once processor 162 has the array layout information corresponding to the read first copy of the local identifier 356, it can then control interrogation of the corresponding array by scanner 160 using such information and/or processing scan information to obtain feature information which is then associated with the layout information. For example, the array layout information could indicate that the scanner need not interrogate specific array addresses for a given test, or alternatively information read from that address can be ignored. Following array interrogation, the test sample can be evaluated for the presence of a target based on the results of the interrogation, either by processor 162 or by a user examining the interrogation results. The results of the evaluation, or alternatively the interrogation results (processed or raw data), could be forwarded to a remote location for further evaluation and/or processing using communication channel 180 or reader/writer 186 and medium 190.

In a variation of the above particular methods, the unique identifier could be omitted from package 340 altogether (printer 350 only printing the corresponding unique identifier on label 354). In this case, following reading of the second copy of the local identifier from the package 340, the corresponding unique identifier could be retrieved from the user station from the remote fabrication station by accessing a database of saved local/unique identifiers in memory 141 through communication channel 180. Further, even the second copy of the local identifier could be omitted from package 340, the read first copy of the local identifier on the array substrate 10 could be used to retrieve the corresponding unique identifier in the foregoing manner. However, use of a package with a label or insert as described, avoids the user station having to contact the remote fabrication station to obtain the foregoing correspondence information, and further avoids the fabrication station having to maintain such data (possibly for a very large number of different remote user stations). Further, in another variation, the second copy of the local identifier could be provided from the fabrication station to the remote user station using the communication channel 180, particularly at the same time corresponding array layout information is being received from the same remote user station. This provision would be in a manner that it could be associated with the corresponding unique identifier by the remote user station (such as by either sending both simultaneously to the remote user station, or by timing).

In another variation, reader/writer 320 at the fabrication station can write onto media 324 the array layout information in association with the corresponding unique identifier and local identifier. This can be enclosed in package 340 as an alternative, or in addition, to the label 354 (if in addition, then media 324 would serve as a backup source of the local identifier and corresponding identifier information).

In addition, it is possible that each array 12 and its substrate 10 may be contained with a housing 400 as illustrated in FIG. 5. Such a housing includes a chamber carrying the substrate which is viewable through a window 402 during interrogation. The chamber is accessible through two ports 404 normally closed by septa. In such a case, the first copy of the local identifier can alternatively be written on housing 400 itself, rather than on substrate 10.

Further modifications in the particular embodiments described above are, of course, possible. For example, where a pattern of arrays is desired, any of a variety of geometries may be constructed other than the organized rows and columns of arrays 12 of FIG. 1. For example, arrays 12 can be arranged in a series of curvilinear rows across the substrate surface (for example, a series of concentric circles or semi-circles of spots), and the like. Similarly, the pattern of regions 16 may be varied from the organized rows and columns of spots in FIG. 2 to include, for example, a series of curvilinear rows across the substrate surface (for example, a series of concentric circles or semi-circles of spots), and the like. Even irregular arrangements of the arrays or the regions within them can be used, at least when some means is provided such that during their use the locations of regions of particular characteristics can be determined (for example, a map of the regions is provided to the end user with the array).

The present methods and apparatus may be used to deposit biopolymers or other moieties on surfaces of any of a variety of different substrates, including both flexible and rigid substrates. Preferred materials provide physical support for the deposited material and endure the conditions of the deposition process and of any subsequent treatment or handling or processing that may be encountered in the use of the particular array. The array substrate may take any of a variety of configurations ranging from simple to complex. Thus, the substrate could have generally planar form, as for example a slide or plate configuration, such as a rectangular or square or disc. In many embodiments, the substrate will be shaped generally as a rectangular solid, having a length in the range about 4 mm to 200 mm, usually about 4 mm to 150 mm, more usually about 4 mm to 125 mm; a width in the range about 4 mm to 200 mm, usually about 4 mm to 120 mm and more usually about 4 mm to 80 mm; and a thickness in the range about 0.01 mm to 5.0 mm, usually from about 0.1 mm to 2 mm and more usually from about 0.2 to 1 mm. However, larger substrates can be used, particularly when such are cut after fabrication into smaller size substrates carrying a smaller total number of arrays 12. Substrates of other configurations and equivalent areas can be chosen. The configuration of the array may be selected according to manufacturing, handling, and use considerations.

The substrates may be fabricated from any of a variety of materials. In certain embodiments, such as for example where production of binding pair arrays for use in research and related applications is desired, the materials from which the substrate may be fabricated should ideally exhibit a low level of non-specific binding during hybridization events. In many situations, it will also be preferable to employ a material that is transparent to visible and/or UV light. For flexible substrates, materials of interest include: nylon, both modified and unmodified, nitrocellulose, polypropylene, and the like, where a nylon membrane, as well as derivatives thereof, may be particularly useful in this embodiment. For rigid substrates, specific materials of interest include: glass; fused silica, silicon, plastics (for example, polytetrafluoroethylene, polypropylene, polystyrene, polycarbonate, and blends thereof, and the like); metals (for example, gold, platinum, and the like).

The substrate surface onto which the polynucleotide compositions or other moieties is deposited may be smooth or substantially planar, or have irregularities, such as depressions or elevations. The surface may be modified with one or more different layers of compounds that serve to modify the properties of the surface in a desirable manner. Such modification layers, when present, will generally range in thickness from a monomolecular thickness to about 1 mm, usually from a monomolecular thickness to about 0.1 mm and more usually from a monomolecular thickness to about 0.001 mm. Modification layers of interest include: inorganic and organic layers such as metals, metal oxides, polymers, small organic molecules and the like. Polymeric layers of interest include layers of: peptides, proteins, polynucleic acids or mimetics thereof (for example, peptide nucleic acids and the like); polysaccharides, phospholipids, polyurethanes, polyesters, polycarbonates, polyureas, polyamides, polyethyleneamines, polyarylene sulfides, polysiloxanes, polyimides, polyacetates, and the like, where the polymers may be hetero- or homopolymeric, and may or may not have separate functional moieties attached thereto (for example, conjugated), Various other modifications to the embodiments of the particular embodiments described above are, of course, possible. Accordingly, the present invention is not limited to the particular embodiments described in detail above.

What is claimed is:

1. A method of generating an addressable array of biopolymers on a substrate, comprising:
    (a) receiving from a remote station, information on a layout of the array and an associated first identifier;
    (b) generating a local identifier corresponding to the first identifier and associated array layout information, the local identifier being shorter in length than the corresponding first identifier;
    (c) fabricating the addressable array on the substrate in accordance with the received layout information;
    (d) applying a first copy of the local identifier to the substrate or a housing carrying the substrate;
    (d) shipping the fabricated array and the first copy of the local identifier to a remote station; and
    (e) forwarding a second copy of the corresponding local identifier to the remote station such that the local identifier is associated with the corresponding first identifier.

2. A method according to claim 1 wherein the first identifier is unique.

3. A method according to claim 1 wherein the biopolymers are polynucleotides.

4. A method according to claim 1 wherein the biopolymers are DNA.

5. A method according to claim 1 wherein the second copy of the local identifier is forwarded to the remote station in association with the corresponding first identifier.

6. A method according to claim 5 wherein the second copy of the local identifier is applied to a same medium to which the corresponding first identifier is applied.

7. A method according to claim 1 wherein the second copy of the local identifier is shipped to the remote station on or in the same package with the corresponding first identifier and the fabricated array.

8. A method according to claim 7 wherein the second copy of the local identifier and first identifier are present together on a packaging containing the fabricated array.

9. A method according to claim 1 wherein a second copy of the local identifier is communicated to the remote station.

10. A method according to claim 1 wherein the array and the first copy of the corresponding local identifier are shipped to the same remote station from which the corresponding first identifier and the layout information were received.

11. A method according to claim 1 wherein the array and the first copy of the corresponding local identifier are shipped to a remote station different from that from which the corresponding first identifier and the layout information were received.

12. A method according to claim 1, additionally comprising saving the received first identifiers in a memory each in association with the corresponding local identifier.

13. A method according to claim 12 additionally comprising saving array layout information for each array in a memory, in association with the corresponding local identifier.

14. A method of generating, at a central fabrication station, addressable arrays of biopolymers on multiple substrates, comprising:
(a) receiving from each of multiple remote stations, information on a layout of an array and an associated first identifier;
(b) for each received first identifier and associated array, generating a local identifier corresponding to the first identifier and associated array, the local identifier being shorter in length than the corresponding first identifier;
(c) fabricating an addressable array on the substrate in accordance with each received layout information;
(d) applying a first copy of each local identifier to the substrate or a housing carrying the substrate, which substrate carries the array corresponding to the generated local identifier;
(d) shipping each of the fabricated arrays and the first copy of the corresponding local identifier to one or more of the remote stations; and
(e) forwarding a second copy of each corresponding local identifier to a remote station such that the local identifier is associated with the corresponding first identifier.

15. A method according to claim 14 wherein the first identifier is unique.

16. A method according to claim 14 additionally comprising applying a second copy of each local identifier and corresponding first identifier to a same medium, and shipping the medium and corresponding array to the same remote station from which the corresponding first identifier was received.

17. A method according to claim 14 wherein a second copy of each local identifier is communicated to the remote station from which the corresponding first identifier was received.

18. A method according to claim 14, additionally comprising at the central fabrication station, saving received first identifiers in a memory each in association with the corresponding local identifiers.

19. A method according to claim 18 additionally comprising saving array layout information for each array in a memory in association with the corresponding local and first identifiers.

20. A computer program product, comprising: a computer readable storage medium having a computer program stored thereon for performing, when loaded into a computer communicating with a fabricator to fabricate an addressable array on the substrate, the steps of:
(a) receiving from a remote station, information on a layout of the array and an associated first identifier;
(b) generating a local identifier corresponding to the first identifier and associated array, the local identifier being shorter in length than the corresponding first identifier;
(c) controlling fabrication of the addressable array on the substrate in accordance with the received layout information;
(d) applying a first copy of the local identifier to the substrate or a housing carrying the substrate; and
(e) generating a second copy of the corresponding local identifier and forwarding the second copy to the remote station such that the local identifier is associated with the corresponding first identifier.

21. A computer program product according to claim 20 wherein the second copy is forwarded to the remote station by communication to the remote station.

22. A computer program product according to claim 20 wherein the second copy is forwarded by writing to a same medium as the corresponding first identifier for shipping to the remote station.

* * * * *